United States Patent
Ollat et al.

(10) Patent No.: US 6,510,739 B1
(45) Date of Patent: Jan. 28, 2003

(54) APPARATUS FOR CONTINUOUSLY MONITORING LIQUID LEVEL CONDITIONS IN A LIQUID-VAPOR SEPARATING DEVICE

(75) Inventors: Xavier R. Ollat, Bloomfield, CT (US); Joseph W. Quinn, Bloomfield, CT (US); Terry M. Grayson, Granby, CT (US)

(73) Assignee: Alstom (Switzerland) Ltd, Baden (CH)

( * ) Notice: Subject to any disclaimer, the term of this patent is extended or adjusted under 35 U.S.C. 154(b) by 0 days.

(21) Appl. No.: 09/898,614

(22) Filed: Jul. 3, 2001

(51) Int. Cl.[7] .......................... G01N 3/32; G08B 21/00
(52) U.S. Cl. ................... 73/579; 73/1.73; 73/53.04; 73/290 V; 340/618
(58) Field of Search ................. 73/579, 290 V, 73/54.41, 32 A, 1.16, 1.15, 1.73, 53.04, 54.01, 54.25, 290 R; 340/618

(56) References Cited

U.S. PATENT DOCUMENTS

| | | | |
|---|---|---|---|
| 4,127,028 A | * 11/1978 | Cox et al. ................. | 73/194 B |
| 4,371,382 A | * 2/1983 | Ross ............................. | 159/49 |
| 4,765,945 A | * 8/1988 | Walleser ....................... | 73/299 |
| 4,861,560 A | * 8/1989 | Nakajima .................... | 422/111 |
| 5,249,551 A | * 10/1993 | Kirpatrick ................ | 122/451.1 |
| 5,406,915 A | * 4/1995 | Kirkpatrick ............... | 122/451.1 |
| 5,559,293 A | * 9/1996 | Kirkpatrick ............... | 122/451.1 |
| 5,578,994 A | * 11/1996 | Cherek et al. .............. | 340/618 |
| 5,831,149 A | * 11/1998 | Webb ....................... | 73/40.5 R |
| 5,881,207 A | * 3/1999 | DeBourg et al. ............ | 392/401 |
| 5,895,848 A | * 4/1999 | Wilson et al. ............ | 73/290 V |
| 6,044,694 A | * 4/2000 | Anderson et al. .......... | 73/54.41 |
| 6,272,921 B1 | * 8/2001 | Ivanovich et al. ........ | 73/290 V |

* cited by examiner

Primary Examiner—Hezron Williams
Assistant Examiner—Jacques Saint-Surin
(74) Attorney, Agent, or Firm—Russell W. Warnock (57) ABSTRACT

An apparatus 100 for providing information concerning a condition of a vessel such as a steam drum 12 which segregates steam and liquid from one another includes a liquid contact assembly 102, a signal generator element 130, and a housing 112 and a conduit 114 for enclosing the signal generator element 130 in a substantially leak proof manner within the vessel space. The liquid contact assembly 102 is disposable at a first vessel location in the steam drum 12 and has a vibration component 108 operable to vibrate at natural frequencies which vary as a function of a predetermined characteristic of the liquid at the first vessel location and a support component 110 for supporting the water contact assembly 102 in contact with the liquid at the first vessel location. The signal generator element 130 generates a signal indicative of a natural frequency of the vibration component 108.

9 Claims, 6 Drawing Sheets

APPARATUS FOR CONTINUOUSLY MONITORING LIQUID LEVEL CONDITIONS IN A LIQUID-VAPOR SEPARATING DEVICE

BACKGROUND OF THE INVENTION

The present invention relates to an apparatus for continuously monitoring liquid level conditions in a liquid-vapor separating device.

In the field of separating vapors and liquids from one another, there are many two-phase mixtures which are to be separated from one another such as the separation of steam from water in a boiler and other two-phase mixtures such as natural gas and hydrocarbons. Steam drums are one type of liquid-vapor separating device which are widely used for separating and drying steam.

Steam generated in a subcritical pressure drum type boiler is intimately mixed with large and variable amounts of circulating boiler water. Before the steam leaves the boiler and enters the superheater, practically all of this associated boiler water must be separated from the steam. This separation must be done within a limited space in the steam drum, within a matter of seconds and under a variety of velocity, pressure and other operating conditions. The pressure drop across the steam and water separators must be kept to a minimum so as not to affect the boiler circulation or water level controls.

The drum of a subcritical pressure boiler serves several functions, the first being that of collecting the mixture of water and steam discharged from the boiler circuits. Also, the drum houses equipment to separate the steam from the water and then purify the steam after it has been separated. The drum internals in subcritical pressure boilers not only separate water from steam but also direct the flow of water and steam to establish an optimum distribution of fluids in the boiler during all loads of boiler operation. The internals may consist of baffles which change the direction of flow of a steam and water mixture, impellers and separators which use a spinning action for removing water from steam or moisture coalesces such as screen and corrugated plate final dryers. These devices are used singly or in consort to separate and purify the steam and remove impurities from the steam leaving the boiler drum.

Failure to control the water level in the drum can lead to damage of the boiler. For example, if the water level becomes too low, the drum interior may be heated excessively, resulting in warpage or plastic deformation of the drum. Moreover, an excessive pressure condition in the drum may result. If the water level becomes too high, vapor may exit the drum which is not sufficiently dry for the next following operation—i.e., there will be excessive moisture carryover. If, for example, a next following operation involves the flow of the vapor into the tubes of a superheater, thermal stress damage may occur or, if a next following operation involves flow of the vapor over the blades of a turbine, the insufficiently dry vapor may undesirably corrode the turbine components.

It is known to calculate a variation or imbalance between the flow of vapor or a liquid vapor mixture into a drum (referred to as inlet flow) and the flow of separated vapor from the drum (referred to as outlet flow) and to evaluate this variation or imbalance of the inlet-outlet flow for the purpose of estimating the water level in the drum. It is further known to coordinate the operation of the drum or the boiler or other device which supplies the liquid-vapor mixture to the drum as a function of the estimated water level including, for example, coordinating the operation of the boiler to de-activate or "trip" the boiler in the event that it is determined that a water level exists which is below a preestablished minimum. A system is described, for example, in U.S. Pat. No. 4,433,646, for performing such a boiler "trip".

It is also known to monitor the water level in a steam drum by monitoring the water level in a reference receptacle. For example, Japanese Patent Publication 06 27 2804 A2 discloses a reference level which is monitored by a water level transmitter.

In spite of the efforts to provide devices capable of monitoring water level conditions in a liquid-vapor separation drum, as evidenced by the conventional devices mentioned hereinabove, there still exist shortcomings in such conventional devices which render the monitoring of drum water level conditions less than satisfactory. For example, such conventional devices oftentimes are only capable of sensing a minimum and/or a maximum water level in the drum, whereby the absence of any warning of an impending minimum or maximum water level condition forecloses the possibility to undertake a corrective water level adjustment; instead, the sensing of such a minimum or maximum water level typically requires that a boiler trip or other operation interruption be undertaken to prevent damage to the drum. Also, the sensing of the water level in a drum by an indirect method such as by the use of a reference water level undesirably adds to the costs and complexity of the drum operation.

Thus, the need still exists for an apparatus capable of providing information concerning the water level conditions in a liquid-vapor separation drum which could directly sense or monitor the actual water level conditions. Moreover, the need still exists for such an apparatus which could not only sense minimum or maximum water level conditions but could also continuously sense actual water level conditions across a predetermined range of water levels bounded by a minimum water level and a maximum water level.

SUMMARY OF THE INVENTION

It is one object of the present invention to provide a vessel condition monitoring apparatus which is capable of providing information concerning the water level conditions in a liquid-vapor separation vessel by directly sensing or monitoring the actual water level conditions in the vessel.

It is another object of the present invention to provide a vessel condition monitoring apparatus which continuously senses actual water level conditions in the vessel being monitored across a predetermined range of water levels bounded by a minimum water level and a maximum water level.

These and other objects of the present invention are provided, in accordance with one aspect of the present invention, by an apparatus for providing information concerning a condition of a vessel such as a steam drum which segregates steam and water from one another, whereby the apparatus includes a first water contact assembly, a signal generator element, and a housing and a conduit for enclosing the signal generator element in a substantially leak proof manner within the vessel space.

In accordance with further details of the one aspect of the present invention, the first water contact assembly is disposable at a first vessel location in the vessel and has a first vibration component operable to vibrate at natural frequencies which vary as a function of a predetermined characteristic of the water at the first vessel location and a first support component for supporting the first water contact assembly in contact with the water at the first vessel location. Also, the signal generator element is operable to generate a signal indicative of a natural frequency of the first vibration component.

In accordance with additional details of the one aspect of the present invention, the vessel condition monitoring apparatus of the present invention includes vessel remote signal receipt means for receiving the signal generated by the first signal generating means at a location outside the vessel enclosed space. Additionally, the vessel condition monitoring apparatus of the present invention includes a signal transmitting element extending between the first signal generating means in the enclosed vessel space and the vessel remote signal receipt means outside the vessel enclosed space. The vessel condition monitoring apparatus of the present invention additionally preferably includes a conduit through which extends the signal transmitting element, the conduit being sealingly connected to the first enclosing means and being substantially leak proof such that the infiltration of water from the enclosed vessel space into the conduit and the first enclosing means is substantially prevented.

The vessel condition monitoring apparatus of the present invention, in accordance with the one aspect of the present invention, monitors the depth of the water. In this connection, the first vibration component preferably includes a tuning fork oriented to vibrate at a natural frequency which varies as a function of the depth of the water in the enclosed vessel space.

In accordance with another aspect of the present invention, there is provided a second water contact assembly disposable at a second vessel location in the vessel spaced from the first vessel location and having a second vibration component operable to vibrate at natural frequencies which vary as a function of a predetermined characteristic of the water at the second vessel location and a second support component for supporting the second water contact assembly in contact with the water at the second vessel location and the signal generator means is operable to generate a signal indicative of at least one natural frequency of the second vibration component of the second water contact assembly.

DETAILED DESCRIPTION OF THE PREFERRED EMBODIMENT

The one embodiment of the vessel condition monitoring apparatus of the present invention is operable to provide information concerning a condition of a vessel operable to segregate liquid and vapor from one another. Although the invention is applicable to the separation of various liquid-vapor mixtures as previously stated, the invention will be described with particular reference to steam drums and the separation of liquid and vapor.

Figure 1:
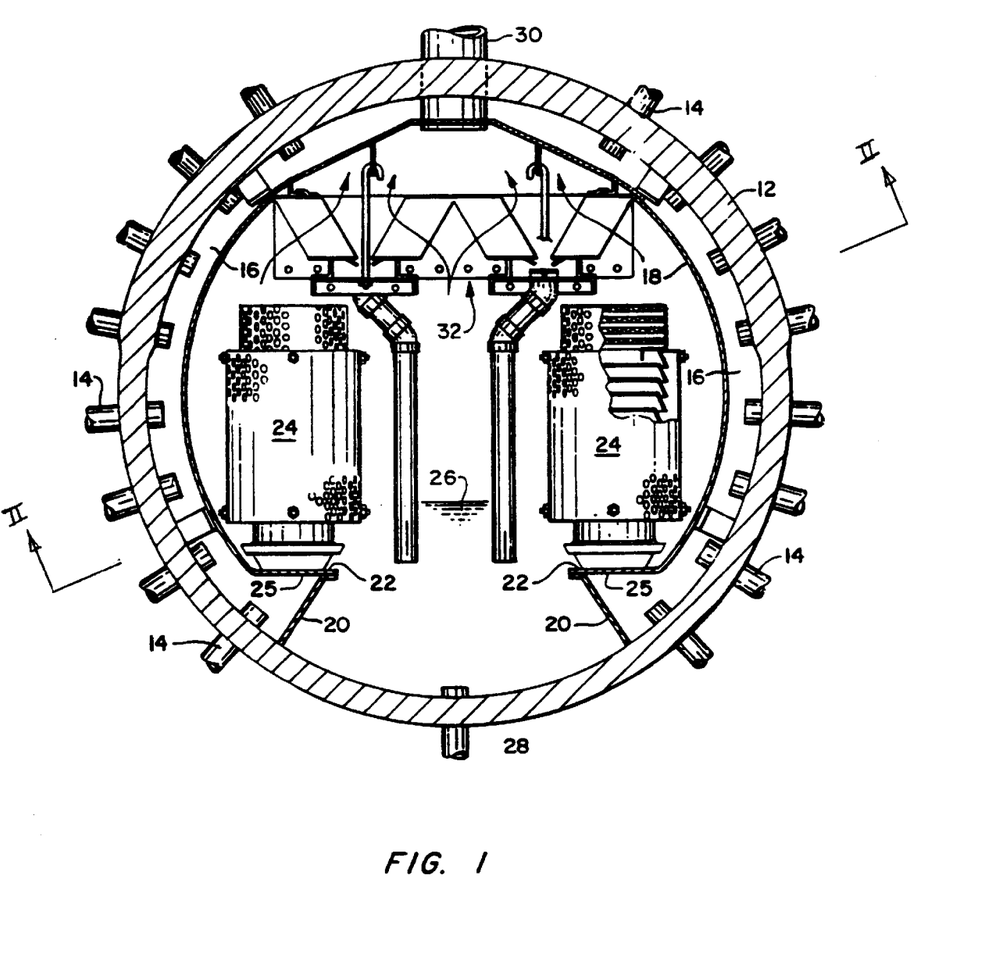
FIG. 1 is a vertical sectional view of a steam drum incorporating the one embodiment of the vessel condition monitoring apparatus of the present invention.

Referring specifically to FIG. 1 of the drawings, the drum 12 is the conventional steam drum configuration with an elongated cylindrical shape and disposed with its axis parallel to the horizontal. The drum 12 is penetrated by riser pipes 14 which receive the steam/liquid mixture from the steam generator and discharge this mixture into the annular space 16 between the drum liner or baffle 18 and the drum 12. Although the riser pipes 14 have been illustrated as being distributed rater uniformly around the annular space 16, the actual sections of the drum penetrated by the risers is a variable that depends on the drum operating pressure, the type of furnace circulation and the mass loading of steam and liquid into the drum. The baffle 18 is closed off at the bottom ends by the baffle portions 20 and the baffle includes the horizontal ledge portions 22. This baffle 18 including its portions 20 and 22 extends the full length of the drum thereby providing the enclosed annular space 16.

Mounted on the baffle ledge portions 22 are a plurality of steam separating units 24 in two horizontally extending rows on either side of the axis of the drum. Although two rows have been illustrated, there may be more than two. Each row would contain as many separators as desired and would be dependent on the drum size and capacity. The steam separators 24 are mounted over apertures 25 in the baffle ledge portions 22 thereby directing the flow of the steam-liquid mixture from the pipes 14 into the annular space 16 and then up through the apertures 25 in the baffle ledge portions 22 and into the interior of the separators 24.

The design details of the steam separators 24 do not constitute a part of the present invention and have not been fully shown. Suffice it to say that the steam separators 24 for purposes of the present invention may be of any conventional design which performs the primary separation of the steam and water and permits the water to drain down from the separators 24 into the pool of water 26 in the bottom of the steam drum. The water then exits the steam drum through the downcomer 28 and is returned to the steam generator. The steam drum would also contain other conventional components which are not shown such as means for providing makeup water, means for introducing chemicals and means for blow-down operation.

The steam which has undergone primary separation from the water in the separators 24 rises through the vapor space in the steam drum towards the steam outlet 30. Located in the vapor space between the separators 24 and the outlet 30 is the final dryer assembly generally indicated as 32.

A more detailed description of the one embodiment of the vessel condition monitoring apparatus of the present invention, which is hereinafter designated as the vessel condition monitoring apparatus 100, is now provided with particular reference to FIG. 2, which is a longitudinal sectional view of the steam drum 12 shown in FIG. 1. In connection with the description of the one embodiment of the vessel condition monitoring apparatus of the present invention, it is to be understood that the steam drum 12 is representative of the type of cylindrical vessel for which the one embodiment of the vessel condition monitoring apparatus of the present invention is suitable in that the drum 12 has an elongate cylindrical body portion, an inlet means for receiving a mixture of liquid and vapor, vapor outlet means in the upper portion thereof for discharging separated vapor and liquid outlet means in the lower portion thereof for discharging separated liquid.

Figure 2:
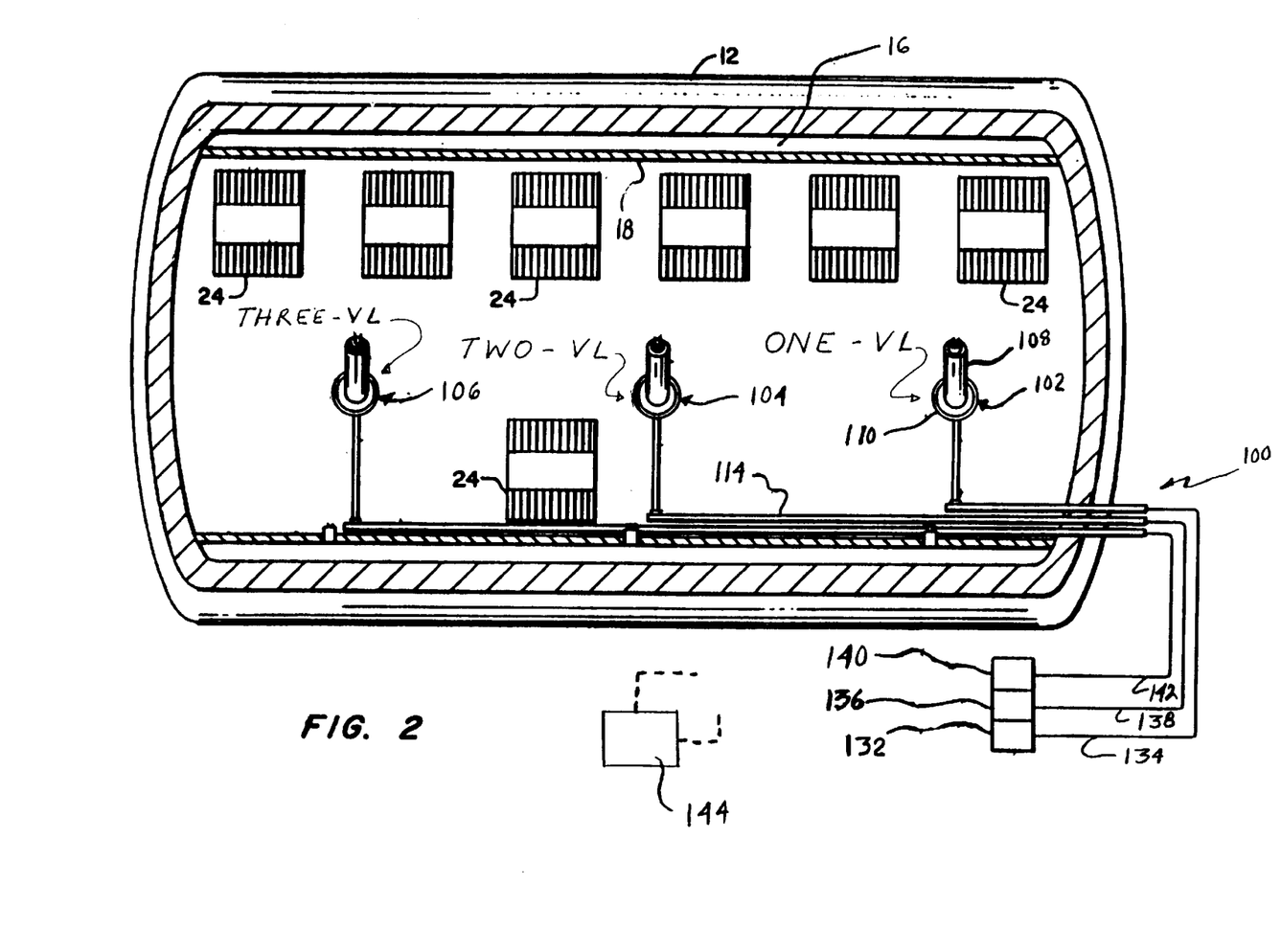
FIG. 2 is a sectional view of the steam drum shown in FIG. 1 taken along line II—II thereof.

As seen in FIG. 2, the vessel condition monitoring apparatus 100 includes a first water contact assembly 102 disposed at a first vessel location ONE-VL in the steam drum 12, a second water contact assembly 104 disposed at a second vessel location SECOND-VL in the steam drum 12, and a third water contact assembly 106 disposed at a third vessel location THIRD-VL in the steam drum 12.

Figure 3:
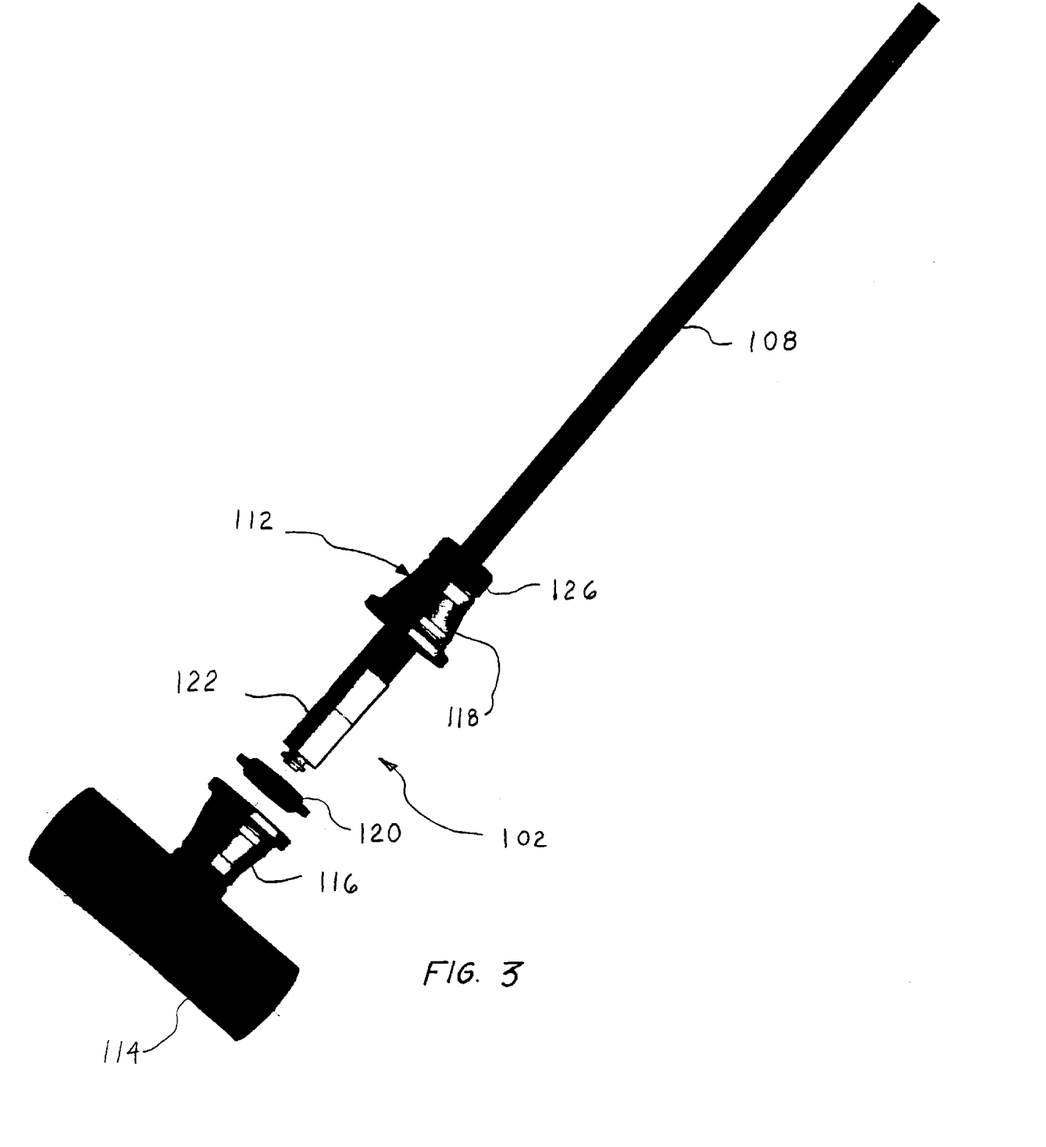
FIG. 3 is an exploded enlarged perspective view of a water contact assembly of the one embodiment of the vessel condition monitoring apparatus of the present invention shown in FIG. 1.
Figure 4:
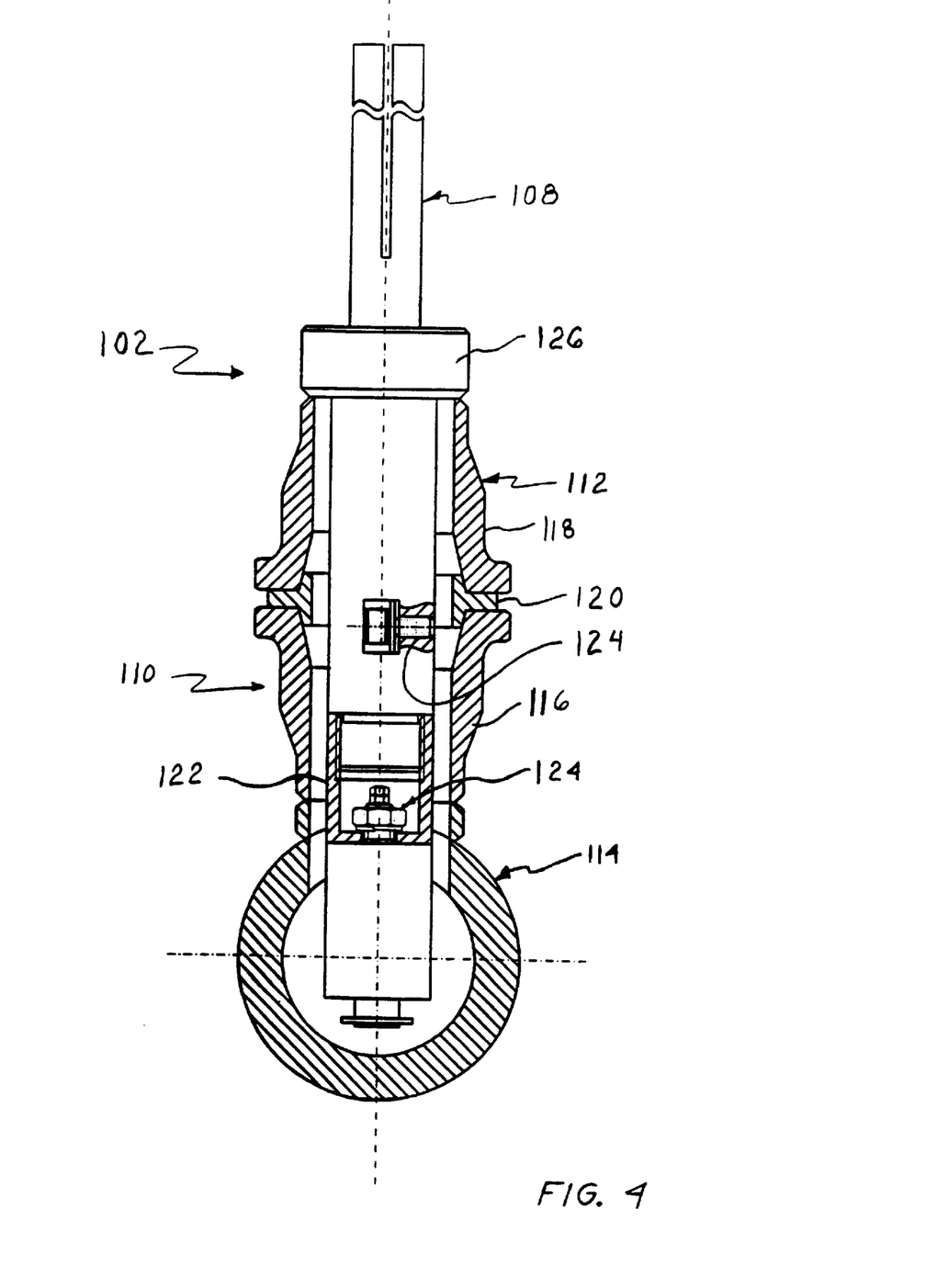
FIG. 4 is an enlarged sectional view of a portion of the water contact assembly shown in FIG. 3.

In connection with the description of the first water contact assembly 102, the second water contact assembly 104, and the third water contact assembly 106, the features and operation of the first water contact assembly 102 will now being described in detail, it being understood that the second water contact assembly 104 and the third water contact assembly 106 are identically configured and operated. Reference is now had to FIG. 3, which is an exploded perspective view of the first water contact assembly 102, and FIG. 4, which is an enlarged sectional view of the first water contact assembly 102 taken along line IV—IV in FIG. 3, in which it can be seen that the first water contact assembly 102 includes a first vibration component, preferably in the form of a tuning fork 108, operable to vibrate at natural frequencies which vary as a function of a predetermined characteristic of the water at the first vessel location ONE-VL. The tuning fork 108 is supported in an upright position generally perpendicular to the water surface level of the water pool 26 by a first support component 110 for supporting the first water contact assembly 102 in contact with the water at the first vessel location ONE-VL. The first support component 110 comprises a housing 112, as best seen in FIG. 4, which is fixedly seated on a conduit 114. The conduit 114 extends to a free end 116, as seen in FIG. 2, which is exterior of the steam drum 12. The housing 112 includes a base housing portion 116 which is fixedly connected by, for example, welding or a suitable threaded connector, to the conduit 114, a cap housing portion 118, and a housing gasket 120.

The first support component 110 further comprises a sleeve 122 for receiving the base of the tuning fork 108 inserted therein and a bolt and nut assembly 124 which fixedly secures the sleeve 122 to the conduit 114. A ring 126 mounted at the top of the sleeve 122 extends circumferentially radially, with respect to the longitudinal axis LA of the tuning fork 108, beyond the circumference of the sleeve 122 and engages the top of the cap housing portion 118, whereby the base housing portion 116 and the cap housing portion 118 compress the housing gasket 120 therebetween due to the axial force in one direction exerted on the cap housing portion 118 by the ring 126 and the axial force in the opposite direction exerted on the base housing portion 116 by the conduit 114.

The first water contact assembly 102 includes a solenoid 124 connected by a power cord 126 extending from the solenoid 124 through the conduit 114 to connect the solenoid 124 with a power source 128 outside of the steam drum 12. The solenoid 124 is operable to deliver an impact to the tuning fork 108 to cause vibration thereof. The first water contact assembly 102 further includes a first means for generating a signal indicative of a natural frequency of the first vibration component which is preferably in the form of a conventional tuning fork signal generator 130 operatively connected to the tuning fork 108. The signal generator 130 is enclosed in a leak proof manner in the housing 112 which operates in this function as a means for enclosing the first signal generator means in a substantially leak proof manner within the steam drum 12.

The vessel condition monitoring apparatus 100 also includes a vessel remote signal receipt means for receiving the signal generated by the first signal generating means at a location outside the vessel enclosed space which is preferably in the form of a first signal evaluation unit 132, as seen in FIG. 2, which is operatively connected via a signal transmitting element in the form of a wire 134 extending between the signal generator 130 in the enclosed vessel space and the vessel remote signal receipt means outside the vessel enclosed space namely, the first signal evaluation unit 132.

The conduit 114 is sealingly connected to the housing 112 and is substantially leak proof such that the infiltration of water from the enclosed vessel space into the conduit and the housing 112 is substantially prevented.

The tuning fork 108 is oriented to vibrate at a natural frequency which varies as a function of the depth of the water pool 26 in the steam drum 12. Thus, the tuning fork 108 provides information concerning a predetermined characteristic of the water—namely, the depth of the water pool 26. The first signal generator 130 generates an electric signal which varies as a function of the natural frequency of the tuning fork 108 and the wire 134, which operates as an electric signal transmission path, transmit signals concerning the vibrations of the tuning fork 108 to the first signal evaluation unit 132.

The vessel remote signal receipt means is also operable to receive signals generated by the second water contact assembly 104 and the third water contact assembly 106 at locations outside the vessel enclosed space and, in this connection, the vessel remote signal receipt means includes a second signal evaluation unit 136, as seen in FIG. 2, which is operatively connected via a signal transmitting element in the form of a wire 138 extending between a second signal generator associated with the second water contact assembly 104 and the second signal evaluation unit 136. Likewise, the vessel remote signal means includes a third signal evaluation unit 140 which is operatively connected via a wire 142 with the third signal generator associated with the third water contact assembly 106.

As seen in FIG. 2, a controller 144, which may be, for example, a personal computer (PC) based controller or a programmable logic controller (PLC), is operatively connected to the solenoids 124 for controlling the actuation of these solenoids.

The operation of the vessel condition monitoring apparatus 100 to provide information concerning water level conditions in the drum 12 is as follows. The heights of the tuning forks 108 are selected such that each tuning fork is at least partially submerged within a predetermined range of water levels which is bounded, on the one hand, by a minimum acceptable water level for the liquid vapor separation operation performed by the drum 12 and, on the other hand, by a maximum acceptable water level for the drum operation. If desired, the heights of the tuning forks 108 can be selected such that the tuning forks remain fully submerged throughout the predetermined water level range.

During the liquid-vapor operation in the drum 12 in which liquid and vapor such as steam are separated from one another for subsequent segregated passage out of the drum through the respective vapor and liquid outlet means, the vessel condition monitoring apparatus 100 is operated to monitor the water level conditions in the drum 12 and to provide information concerning these water level conditions. The solenoids 124 are actuated in a selected manner by the controller 144 to effect vibration of the respective tuning forks 108. The solenoids 124 may be actuated, for example, in a pattern in which all of the solenoids are actuated at the same cyclic time at uniform time intervals or in a pattern in which all of the solenoids are actuated at the same time but at varying time intervals between actuations. Alternatively, the solenoids 124 may be actuated independent of one another at respective individual uniform time intervals or respective individual non-uniform time intervals.

Each solenoid 124 impacts the respective associated tuning fork 108 with substantially the same force upon each actuation of the solenoid, whereby the vibration of the tuning fork varies as a function of the water level at the tuning fork location in that the dampening effect of the water in which the tuning fork is partially or fully submerged on the tuning fork varies in correspondence with the depth of the water. Information concerning the tuning fork vibrations such as, for example, information relating to the amplitude or frequency of the vibrations, is relayed via the wires 134, 138, and 142 to the respective remote signal evaluation unit 132, 136, and 140, respectively. The signal evaluation units 132, 136, and 140 are preferably operatively connected to the controller 144 which has a capability to provide an output in a suitable audio or visual format for advising the boiler operator concerning the drum water level and/or has a capability to control, or provide a signal for controlling, the operation of the boiler and/or the drum in response to the monitored drum water level.

The one embodiment of the vessel condition monitoring apparatus of the present invention shown in FIGS. 1–4 includes separate conduits 114 each associated with a respective one of the first water contact assembly 102, the second water contact assembly 104, and the third water contact assembly 106. In a variation of the one embodiment of the vessel condition monitoring apparatus of the present invention shown in FIG. 5, the vessel condition monitoring apparatus is identical to the one embodiment of the vessel condition monitoring apparatus shown in FIGS. 1–4 except that the separate conduits 114 are omitted in this one variation in lieu of a single common conduit 214 onto which each of one of the first water contact assembly 102, the second water contact assembly 104, and the third water contact assembly 106 is mounted. The common conduit 214 extends exteriorly of the drum 12 such that the respective wires 134, 138, and 142 all extend within the common conduit 214 from the respective water contact assembly to the respective signal evaluation unit 132, 136, 140 which is located exteriorly of the drum 12.

Figure 5:
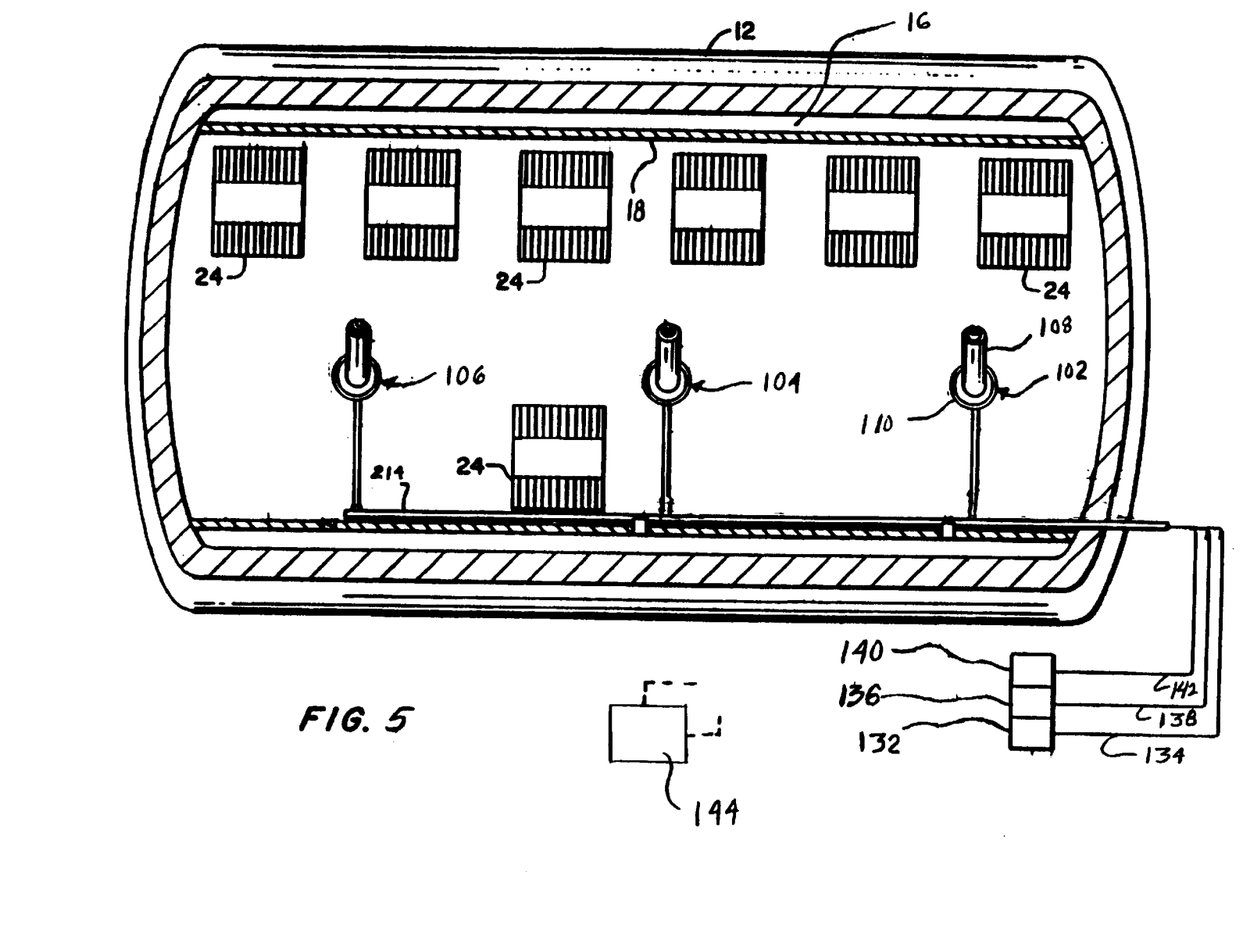
FIG. 5 is a sectional view of a steam drum incorporating a variation of the one embodiment of the vessel condition monitoring apparatus of the present invention.

It can be seen that each one of the first water contact assembly 102, the second water contact assembly 104, and the third water contact assembly 106, together with its respective separate conduit 114, in the one embodiment of the vessel condition monitoring apparatus of the present invention shown in FIGS. 1–4, or together with the common conduit 214 in the variation of the one embodiment of the vessel condition monitoring apparatus of the present invention shown in FIG. 5, forms a leak proof unit which protects the enclosed components such as the solenoid 124 or the wire 134, 138, 142 from the hostile environment of the drum 12. In particular, these components are protected from direct contact with the water in the drum 12 which typically has a temperature of between 70 degrees Fahrenheit to 700 degrees Fahrenheit.

The present invention also contemplates that the vibration or excitation of the tuning forks 108 can be effected as well by another suitable configuration in lieu of the individual solenoid configuration of the one embodiment of the vessel condition monitoring apparatus of the present invention shown in FIGS. 1–4. For example, the tuning forks 108 can be arranged at a distance from one another such the vibration of one of the tuning forks (effected by, for example, a solenoid) can effect vibration of one or more proximate tuning forks, whereby the need for a separate mechanical or electrical actuator such as a solenoid for the proximate tuning forks can be dispensed with. Also, the present invention contemplates that structures other than tuning forks which can be induced to vibrate in vibratory cycles can be used as well.

Figure 6:
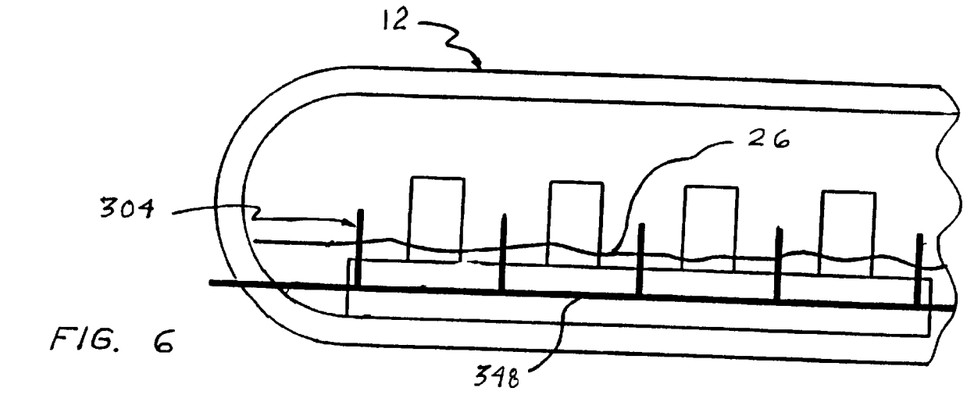
FIG. 6 is a side sectional schematic view of a portion of a steam drum having a further variation of the one embodiment of the vessel condition monitoring apparatus of the present invention.
Figure 7:
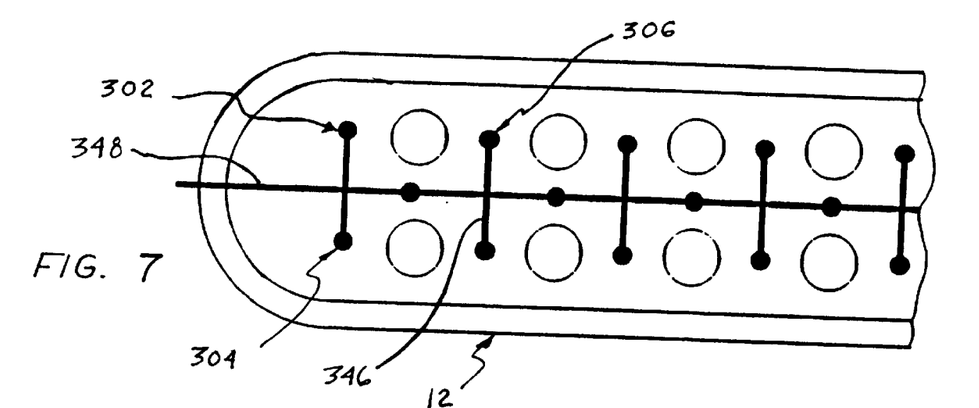
FIG. 7 is a top plan view of the portion of the steam drum having a further variation of the one embodiment of the vessel condition monitoring apparatus of the present invention shown in FIG. 6.

FIG. 6 is a side sectional schematic view, and FIG. 7 is a top plan view, of a portion of the steam drum 12 having a further variation of the one embodiment of the vessel condition monitoring apparatus of the present invention. In this further variation of the one embodiment of the vessel condition monitoring apparatus 100, a plurality of water contact assemblies are each mounted on a branch conduit 346 which are all commonly communicated with a common trunk conduit 348 extending parallel to the longitudinal axis of the steam drum 12 generally at the lateral mid plane thereof. Thus, each one of a first water contact assembly 302, a second water contact assembly 304, and a third water contact assembly 306, as well as the other water contact assemblies, is identically configured to, and operated in the same manner as, the first water contact assembly 102, and is disposed at the distal end of a respective branch conduit 348. The water contact assemblies are each offset from another respective water contact assembly to an opposite lateral side of the common trunk conduit 348; for example, the first water contact assembly 302 is longitudinally aligned with, and laterally offset from, the second water contact assembly 304.

Each of the first water contact assembly 302, the second water contact assembly 304, the third water contact assembly 306, and the other water contact assemblies includes a tuning fork 308 which is partially submerged in the steam drum 12—i.e., the lower portion of the tuning fork is below the water level 26 of the steam drum while the upper portion of the tuning fork is above the water level 26. The common trunk conduit 348 extends exteriorly of the steam drum 12 and, together with the branch conduits 346, provides leak proof, heat shielded protection of the signal wires extending between each water contact assembly and its associated signal evaluation unit.

What is claimed is:

1. An apparatus for providing information concerning a condition of a vessel operable to segregate steam and liquid from one another, comprising:

a first liquid contact assembly disposable at a first vessel location in the vessel and having a first vibration component operable to vibrate at natural frequencies which vary as a function of a predetermined characteristic of the liquid at the first vessel location and a first support component for supporting the first liquid contact assembly in contact with the liquid at the first vessel location;

first means for generating a signal indicative of a natural frequency of the first vibration component; and means for enclosing the first signal generator means in a substantially leak proof manner within the vessel space.

2. An apparatus for providing information concerning a condition of a vessel according to claim 1 and further comprising vessel remote signal receipt means for receiving the signal generated by the first signal generating means at a location outside the vessel enclosed space.

3. An apparatus for providing information concerning a condition of a vessel according to claim 2 and further comprising a signal transmitting element extending between the first signal generating means in the enclosed vessel space and the vessel remote signal receipt means outside the vessel enclosed space.

4. An apparatus for providing information concerning a condition of a vessel according to claim 3 and further comprising a conduit through which extends the signal transmitting element, the conduit being sealingly connected to the first enclosing means and being substantially leak proof such that the infiltration of liquid from the enclosed vessel space into the conduit and the first enclosing means is substantially prevented.

5. An apparatus for providing information concerning a condition of a vessel according to claim 4 wherein the signal generating means generates an electric signal which varies as a function of the natural frequency of the first vibration component and the signal transmitting element includes an electric signal transmission path.

6. An apparatus for providing information concerning a condition of a vessel according to claim 5 wherein the predetermined characteristic of the liquid is the depth of the liquid.

7. An apparatus for providing information concerning a condition of a vessel according to claim 6 wherein the first vibration component includes a tuning fork oriented to vibrate at a natural frequency which varies as a function of the depth of the liquid in the enclosed vessel space.

8. An apparatus for providing information concerning a condition of a vessel according to claim 7 and further comprising a second liquid contact assembly disposable at a second vessel location in the vessel spaced from the first vessel location and having a second vibration component operable to vibrate at natural frequencies which vary as a function of a predetermined characteristic of the liquid at the second vessel location and a second support component for supporting the second liquid contact assembly in contact with the liquid at the second vessel location and the signal generator means is operable to generate a signal indicative of at least one natural frequency of the second vibration component of the second liquid contact assembly.

9. An apparatus for providing information concerning a condition of a vessel according to claim 7 wherein the first liquid contact assembly includes a solenoid operable to deliver an impact to the respective vibration component to cause vibration thereof and a power cord extending from the solenoid through the conduit to connect the solenoid with a power source outside of the vessel.

* * * * *